United States Patent [19]
Hoegnelid et al.

[11] Patent Number: 5,431,172
[45] Date of Patent: Jul. 11, 1995

[54] METHOD FOR DETECTING TACHYARRHYTHMIA OF A HEART BY MEASURING PATIENT ACTIVITY AND PARTIAL PRESSURE OF BLOOD OXYGEN

[75] Inventors: Kurt Hoegnelid, Västerhaninge; Nils Holmstroem, Tennisv.; Pia Hagel, Sollentuna; Agneta Franksson, Stockholm, all of Sweden

[73] Assignee: Pacesetter AB, Solna, Sweden

[21] Appl. No.: 119,532

[22] Filed: Sep. 13, 1993

[30] Foreign Application Priority Data

Sep. 11, 1992 [EP] European Pat. Off. ........... 92115567

[51] Int. Cl.⁶ ............................................. A61N 1/365
[52] U.S. Cl. .................................................... 128/705
[58] Field of Search ............... 128/632, 637, 695, 696, 128/702, 705; 607/9, 14, 17, 19, 22

[56] References Cited

U.S. PATENT DOCUMENTS

| | | |
|---|---|---|
| 3,805,795 | 4/1974 | Denniston et al. |
| 3,942,536 | 3/1987 | Mirowski et al. |
| 4,403,614 | 9/1983 | Engle et al. |
| 4,541,430 | 9/1985 | Elmqvist et al. |
| 4,967,748 | 11/1990 | Cohen. |
| 5,085,213 | 2/1992 | Cohen. |
| 5,119,813 | 6/1992 | Cohen. |
| 5,213,098 | 5/1993 | Bennett et al. ............ 607/18 |

FOREIGN PATENT DOCUMENTS

| | | |
|---|---|---|
| 0191404 | 8/1986 | European Pat. Off. |
| 9215367 | 9/1992 | WIPO ..................... 607/4 |

*Primary Examiner*—William E. Kamm
*Assistant Examiner*—Marianne Parker
*Attorney, Agent, or Firm*—Hill, Steadman & Simpson

[57] ABSTRACT

For detecting tachyarrhythmia of the heart, the partial pressure of gases physically dissolved in the blood is measured, preferably the partial oxygen pressure $pO_2$, and a fast variation and/or a variation of the measured partial pressure $pO_2$ that exceeds a prescribed degree is utilized as a criterion for the detection of a tachyarrhythmia. An apparatus for treating tachyarrhythmia of the heart operating according to the above method includes a sensor for identifying the partial pressure of gases dissolved in the blood, an evaluation unit supplied with the sensor output for recognizing rapid changes of the partial pressure or changes of the partial pressure that exceed a prescribed degree, the output of the evaluation unit being connected to circuitry for triggering the tachyarrhythmia treatment.

16 Claims, 1 Drawing Sheet

METHOD FOR DETECTING TACHYARRHYTHMIA OF A HEART BY MEASURING PATIENT ACTIVITY AND PARTIAL PRESSURE OF BLOOD OXYGEN

BACKGROUND OF THE INVENTION

1. Field Of the Invention

The present invention is directed to a method for detecting tachyarrhythmia of the heart, as well as to an apparatus for treating tachyarrhythmia with means for detecting tachyarrhythmia operating according to the method and having an output connected to means for triggering the tachyarrhythmia treatment.

2. Description of the Prior Art

Tachyarrhythmia are disturbances in the rhythm of the heart exhibiting an unnaturally elevated frequency, caused by pathologies of the stimulus formation or stimulus conduction in the heart. Such tachyarrhythmia lead to a reduced chamber filling and ejection power of the heart and, in the worst case, can lead to a standstill of the blood conveying through the heart given the presence of ventricular fibrillation.

European Patent 0 108 360 discloses that a rapid heart rhythm, when caused by retrograde transfer, can be terminated by electrical stimulation pulses from a heart pacemaker that are delivered to the heart at specific times with reference to the tachycardia heartbeats.

U.S. Pat. No. 4,403,614 discloses an implantable cardioverter, wherein the heart frequency is calculated by measuring the spacing of successive R-waves of the heart. Rhythm disturbances having frequencies of less than 140 beats per minute are thereby classified benign and rhythm disturbances having frequencies between 140 and 300 beats per minute are thereby classified pathological because they develop into ventricular fibrillation, whereas a ventricular fibrillation is assumed to be present if frequencies of more than 300 beats per minute are detected. When a tachyarrhythmia classified as pathological is detected, a cardioversion of the heart is triggered with a cardioversion energy that lies between the standard stimulation energy of heart pacemaker pulses and the energy required for defibrillation purposes. A defibrillation of the heart occurs given the detection of ventricular fibrillation.

The different therapy methods of anti-tachycardia stimulation, cardioversion and fibrillation require a recognition of the rhythm disturbances of the heart. The detection of tachyarrhythmia using only a heartbeat detector and evaluation of heartbeat-frequency-related criteria such as frequency, sudden frequency rise and persistent, high-frequency values can be problematical. In particular, there is the risk that a rapid sinus rhythm will be misinterpreted as tachycardia.

U.S. Pat. No. 3,942,536 discloses an implantable cardioverter, wherein the pressure in the right ventricle is acquired with a pressure sensor at the end of a catheter; as soon as the measured pressure drops below a limit value over a prescribed chronological duration, a cardioversion of the heart is triggered. Heretofore, however, the production of pressure sensors that are adequate for this purpose has not succeeded, in part because of the difficulty of devising a pressure sensor which is insensitive enough so that the measured results thereof are not falsified by the deposits of fibrous tissue, but which has sufficient sensitivity so that static pressures can also be precisely measured.

It is proposed in U.S. Pat. No. 3,805,795 to utilize, for example, the heartbeat frequency acquired with a heartbeat detector as a first criterion and to utilize the mechanical heart activity acquired with a motion sensor in the heart as a second criterion for the detection of tachyarrhythmia, and to trigger a shock treatment of the heart when both criteria are simultaneously met over a prescribed chronological duration.

U.S. Pat. No. 5,085,213 discloses an implantable defibrillator/cardioverter, wherein pressures measured in the heart and frequency criteria are utilized for identifying disturbances in heart rhythm. As in the aforementioned U.S. Pat. No. 3,942,536, suitable pressure sensors having adequate long-term stability have hitherto not been available, particularly for the measurement of static pressures.

SUMMARY OF THE INVENTION

It is an object of the present invention to provide a method and apparatus which enable reliable detection of harmful tachyarrhythmia of the heart.

This object is achieved in a method in accordance with the principles of the present invention wherein the partial pressure of gases physically dissolved in the blood is measured in vivo, and wherein a rapid change of the measured partial pressure and/or a change of the measured partial pressure that exceeds a prescribed degree is utilized as a criterion for the detection of a tachyarrhythmia.

The object is achieved in an apparatus constructed in accordance with the principles of the present invention means for detecting tachyarrhythmia including a sensor for identifying in vivo the partial pressure of gases dissolved in the blood, and the sensor is followed by an evaluation means for recognizing rapid variation of the measured partial pressure or variation of the measured partial pressure that exceeds a prescribed degree. The apparatus of the invention for treating tachyarrhythmia can be an anti-tachycardia heart pacemaker, converter or defibrillator.

When a tachyarrhythmia episode starts, this causes an extremely rapid drop in pressure in the heart, so that the partial pressure of the gases dissolved in the blood changes very rapidly. By measuring the partial pressure, thus various types of tachyarrhythmia are successfully diagnosed not indirectly via the heartbeat frequency but, by contrast, via their hemodynamic effects. Differing from pressure sensors, sensors for identifying partial pressures can be simply realized as catheter sensors and have a long-term stability. Such sensors for measuring the oxygen concentration are disclosed, for example, U.S. Pat. No. 4,779,618, U.S. Pat. No. 4,853,091, European Application 0 455 072 and PCT Application WO 91/17433.

U.S. Pat. No. 4,779,618 further discloses the employment of such an oxygen sensor for the frequency control of a heart pacemaker, however, the dependency of the oxygen content of the blood on the partial pressure of the oxygen is defined by exploiting a phenomenon referred to as the oxygen bonding curve of the blood. Since, however, only very little oxygen is physically dissolved in the blood, the oxygen content of the blood largely corresponds to the oxygen chemically bonded to hemoglobin, i.e., to the oxygen saturation of the blood which is a metabolic parameter. This is used in this known frequency-controlled heart pacemaker as a stress-dependent regulating variable. Differing therefrom, the partial pressure of the oxygen in the blood is measured in an embodiment of the method of the invention and a rapid drop of the measured partial pressure and/or a drop of the measured partial pressure below a prescribed minimum value is utilized as a criterion for the detection and diagnosis of various tachyarrhythmia. In an embodiment of the apparatus of the invention, consequently, the sensor is fashioned as an oxygen sensor and the evaluation means comprises means for detecting a sudden drop of the measured partial oxygen pressure and/or of a drop of the measured partial oxygen pressure that falls below a prescribed minimum value. Differing from the aforementioned, known heart pacemaker, the phenomenon that the partial pressure of the oxygen in the blood given a sudden drop in pressure in the heart due to tachycardia rhythm disturbances drops rapidly is utilized for the detection and diagnosis of a tachyarrhythmia. When the partial oxygen pressure falls below the prescribed minimum value, this indicates that the blood conveying, and thus the charging of the blood with oxygen, has practically come to a standstill; the presence of ventricular fibrillation is thus detected directly therefrom.

In a further embodiment of the method of the invention, the heartbeat frequency is acquired and interpreted as a further criterion for the detection of a tachyarrhythmia, with the simultaneous presence of both criteria being utilized as the basis for identifying the existence of a tachyarrhythmia. In this context, a heartbeat detector is provided in the apparatus of the invention which is followed by a further evaluation means for identifying the heartbeat frequency, the two evaluation means being connected at their outputs via AND element to the means for triggering the tachyarrhythmia treatment. Tachyarrhythmia are thereby successfully detected and diagnosed on the basis of their frequency as well as on the basis of their hemodynamic effects. The evaluation of the heartbeat frequency thereby ensues in a known way via the EKG of the heart, and can employ criteria such as the presence of an elevated frequency, a sudden rise in frequency or, a persistent elevated frequency.

In a further embodiment of the method of the invention, the physical activity of the patient is acquired with an activity sensor and a low or unmodified, measured activity given simultaneous change of the partial pressure is utilized as a criterion for the detection of a tachyarrhythmia. The detection reliability is thereby further enhanced. An increase in the physical activity leads to an increased oxygen requirement and, thus to a drop in the partial oxygen pressure. When a drop in the partial oxygen pressure is measured without an increase in the physical activity being present, or when the activity level is extremely low at the same time, then a malfunction of the heart that degrades the blood conveying, and thus the oxygen charging of the blood is present.

DESCRIPTION OF THE PREFERRED EMBODIMENTS

Figure 1A:
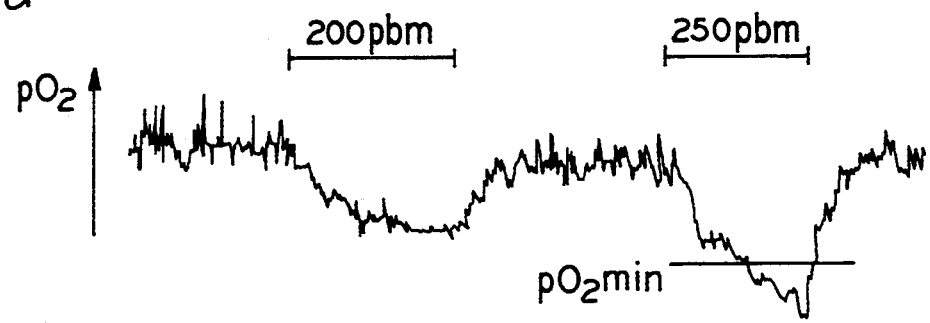
FIG. 1a is a graph showing the behavior of the partial oxygen pressure $pO_2$ in the right atrium given an elevated, stimulated heartbeat frequency.
Figure 1B:
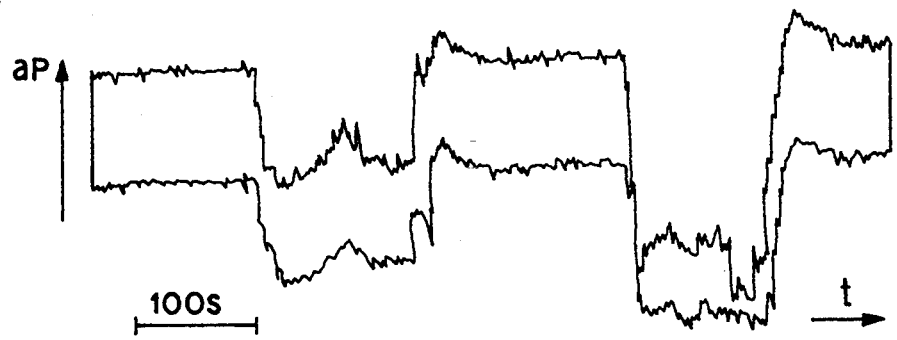
FIG. 1b is a graph showing the behavior of the arterial pressure aP given an elevated, stimulated heartbeat frequency.
Figure 2:
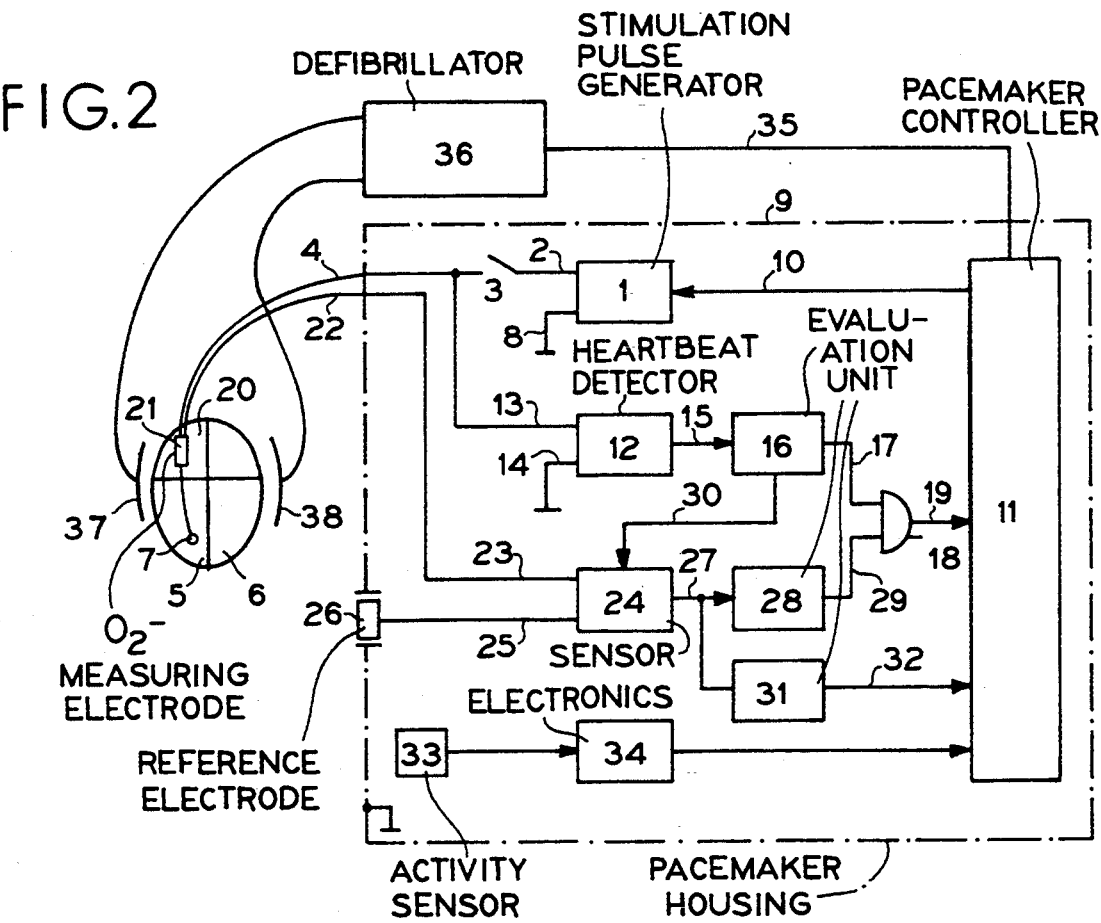
FIG. 2 is a block diagram of an exemplary embodiment of the apparatus of the invention for tachyarrhythmia treatment in the form of an anti-tachycardia heart pacemaker, which practices the method of the invention.

FIG. 1a shows the curve of the partial oxygen pressure $pO_2$ measured in the right atrium of the heart, and FIG. 1b shows the associated curve of the arterial pressure aP, which arise when the beat rate of a spontaneously beating heart is raised by stimulation with a heart pacemaker to 200 beats per minute in a first interval, and to 250 beats per minutes in a second interval. At these high frequency values, the chamber filling and the ejection power of the heart degrades to an extent which cannot be naturally compensated, or can only be inadequately compensated by the circulation control inherent in the body. As FIGS. 1a and 1b 2 show, the stimulation of the heart with frequencies of 200 or 250 beats per minute leads to a sudden arterial pressure drop with a corresponding reaction of the partial oxygen pressure $pO_2$ that is just as rapid. The partial oxygen pressure $pO_2$ is thus a very fast and sensitive quantity for identifying the presence of tachyarrhythmia. In the case of the stimulation with 200 beats per minute, the partial oxygen pressure $pO_2$ stabilizes at a lower level after some time, which is attributed to a reduced blood supply and, thus to a diminished oxygen saturation of the blood. In the stimulation of the heart with 250 beats per minute, by contrast, the partial oxygen pressure $pO_2$ drops continuously because the blood conveying and thus the charging of the blood with, oxygen have practically come to a standstill. The same situation would also occur given a ventricular fibrillation, being detected in accord with the method of the invention in that the partial oxygen pressure $pO_2$ drops below a minimum value $pO_{2min}$.

FIG. 2 shows a block circuit diagram of an anti-tachycardia heart pacemaker wherein the partial pressure of the oxygen $pO_2$ in the blood is utilized for the detection of tachyarrhythmia. The heart pacemaker contains a stimulation pulse generator 1 having an output terminal 2 connected via a controllable switch 3 and an electrode line 4 to a stimulation electrode 7. The stimulation electrode 7 may consist of, for example, activated glass carbon and is arranged in the ventricle 5 of the heart 6. A second output terminal of the stimulation pulse generator 1 is connected to a housing 9 of the heart pacemaker that serves as the cooperating (return) electrode for the stimulation electrode 7. The stimulation pulse generator 1 is connected via a control line 10 to a heart pacemaker controller 11 that initiates the output of stimulation pulses by the stimulation pulse generator 1 via the control line 10. A heartbeat detector 12 for the detection of stimulated or natural electrical heart activities has a first input terminal 13 connected to the stimulation electrode 7 and has a second input terminal 14 connected to the heart pacemaker housing 9. An evaluation unit 16 that evaluates the detected heartbeats with respect to their rate is connected to the output 15 of the heartbeat detector 12. The evaluation unit 16 is connected via an output line 17 to a first input of an AND element 18, which has an output 19 connected to the heart pacemaker controller 11.

An oxygen-measuring electrode 21, preferably consisting of smooth, electrocatalytically inactive glass carbon, is arranged in the right atrium 20 of the heart 6. The electrode 21 is connected via a further electrode line 22 to a first input 23 of sensor electronics 24 which has a second input 25 connected to a silver-silver chloride reference electrode 26. The oxygen-measuring electrode 21 is preferably fashioned as an annular electrode and is spaced in the proximal direction (i.e., in a direction away from the stimulation/measurement site) from the stimulation electrode 7, which is preferably fashioned as a tip electrode. The electrodes 21 and 7 are arranged on a catheter that is shared in common by both electrodes 7 and 21 (not shown).

Alternatively to the illustrated exemplary embodiment, the oxygen-measuring electrode 21 can be additionally utilized for acquiring the heartbeats, in which case the input terminal 13 of the heartbeat detector 12 is connected not to the stimulation electrode 7 but to the oxygen-measuring electrode 21, or the input terminal 14 of the heartbeat detector 12 is connected to the oxygen-measuring electrode 21 instead of to the pacemaker housing 9.

The reference electrode 26 is preferably arranged in the region of the heart pacemaker housing 9, insulated therefrom, but can also be arranged at a catheter. The oxygen sensor formed by the electrodes 21 and 26 and by the sensor electrodes 24 functions such that one or more test voltages between the electrodes 21 and 26 are generated during prescribed times outside the stimulation of the heart 6, and the flow of current resulting therefrom is measured in the oxygen-measuring electrode 21 and is integrated. A value corresponding to the partial oxygen pressure pO$_2$ is thus obtained at the output 27 of the sensor electronics 24. The aforementioned patent publications U.S. Pat. No. 4,779,618, U.S. Pat. No. 4,853,091, European Application 0 445 072 and PCT Application WO 91/17433 can be consulted for further details of partial oxygen pressure measurement.

An evaluation unit 28 in which a sudden drop of the measured value for the partial oxygen pressure pO$_2$ is detected is connected to the output 27 of the sensor electronics 24. The "sudden drop" may be a selected change in the magnitude of the partial pressure over a selected period of time, or may be the occurrence of the magnitude of the partial pressure exceeding a predetermined magnitude change amount, regardless of time. The evaluation unit 28 is connected via an output line 29 to a second input of the AND element 18. In order to reduce the power consumption due to the measurement of the partial oxygen pressure pO$_2$, the sensor electronics 24 is connected via a control line 30 to the evaluation unit 16 following the heartbeat detector 12 and is only activated by the evaluation unit 16 when the measured heartbeat rate exceeds a prescribed value of, for example, 110 beats per minute.

A further evaluation unit 31 connected to the output 27 of the sensor electronics 24 supplies a signal via its output line 32 to the heart pacemaker controller 11 when the measured partial oxygen pressure pO$_2$ falls below the prescribed minimum value pO$_{2min}$. An activity sensor 33 such as, for example, an acceleration sensor, is arranged in the housing 9, and is connected to the heart pacemaker controller 11 via separate sensor electronics 34.

The heartbeat detector 12 detects the heartbeat rate or the rate of selected repetitive characteristics of the electrical activity of the heart 6. The evaluation unit 16 evaluates the measured heartbeat rate and activates the sensor electronics 24 when the prescribed limit frequency of, for instance, 110 beats per minute is upwardly transgressed. Given a further, sudden rise of the heartbeat rate causing an upward transgression of another prescribed limit value during a prescribed duration, the evaluation unit 16 generates an output signal on its output line 17 as criterion indicating the presence of a tachyarrhythmia. The evaluation unit 28 following the sensor electronics 24 generates an output signal on its output line 29 when the measured value for the partial oxygen pressure pO$_2$ suddenly falls below a prescribed limit value, or drops by a prescribed amount within a prescribed time. The output signal of the output line 29 forms a second criterion for the presence of a tachyarrhythmia, which is combined with the first criterion on the output line 17 by the AND element 18 such that the heart pacemaker controller 11 is then informed via the output 19 of the AND element 18 of the presence of a tachyarrhythmia, for example, a tachycardia, when both criteria are simultaneously met. In this case, the heart pacemaker controller 11 commands the stimulation pulse generator 1, via the control line 10, to generate a programmed sequence of stimulation pulses for terminating the tachycardia. Examples of appropriate stimulation sequences for terminating a tachyarrhythmia are disclosed in the previously cited European Application 0 108 360.

When the partial oxygen pressure pO$_2$ drops below the prescribed minimum value pO$_{2min}$, this is detected by the further evaluation unit 31 as the consequence of ventricular fibrillation and the heart pacemaker controller 11 is informed thereof. In response, the controller 11 supplies a control signal via a control line 35 (or via a wireless transmission link as an alternative thereto) to a defibrillator 36 which delivers a defibrillation pulse to the heart 6 via defibrillation electrodes 37 and 38.

A more complete classification of different tachyarrhythmia can, for example, ensue in the manner described in previously cited U.S. Pat. No. 4,403,614 or U.S. Pat. No. 5,085,213, whereby the sudden drop of the partial oxygen pressure in the blood is utilized as additional criterion for the detection of the tachyarrhythmia or as a criterion that is an alternative to measuring the pressure in the heart.

The reliability in the detection of tachyarrhythmia is further enhanced, given a sudden or substantial drop of the partial oxygen pressure pO$_2$, the physical activity of the patient acquired by the activity sensor 33 is utilized by the controller 11 as a check to determine whether the drop of the partial oxygen pressure pO$_2$ is based on an elevated physical activity. When, by contrast, a drop in the partial oxygen pressure pO$_2$ is measured given an unvarying or low physical activity of the patient, then this is a criterion for the presence of a tachycardia.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for detecting tachyarrhythmia of a heart comprising the steps of:
    measuring a partial pressure of gases dissolved in blood of a patient and monitoring any changes of said partial pressure;
    measuring physical activity of said patient, in whom tachyarrhythmia is to be detected, utilizing an activity sensor; and
    utilizing a simultaneous occurrence of a low activity level and presence of a selected change in the measured partial pressure as a criterion for detecting a tachyarrhythmia.

2. A method as claimed in claim 1 wherein the step of utilizing a selected change in the measured partial pressure as a part of the criterion for the detection of a tachyarrhythmia is further defined by utilizing an occurrence of a selected change in magnitude of said measured partial pressure over a selected period of time as a part of the criterion for the detection of a tachyarrhythmia.

3. A method as claimed in claim 1 wherein the step of utilizing a selected change in the measured partial pressure as a part of the criterion for the detection of a tachyarrhythmia is further defined by utilizing an occurrence of the magnitude of said measured partial pressure falling below a predetermined minimum value as a part of the criterion for the detection of a tachyarrhythmia.

4. A method as claimed in claim 1 wherein the step of measuring a partial pressure of gases dissolved in the blood is further defined by measuring a partial pressure of oxygen in the blood.

5. A method as claimed in claim 4 wherein the step of utilizing a selected change in the measured partial pressure as a part of the criterion for the detection of a tachyarrhythmia is further defined by utilizing an occurrence of a decrease in magnitude of the measured partial pressure of oxygen in the blood over a selected period of time as a part of the criterion for the detection of a tachyarrhythmia.

6. A method as claimed in claim 4 wherein the step of utilizing a selected change in the measured partial pressure as a part of the criterion for the detection of a tachyarrhythmia is further defined by utilizing an occurrence of the magnitude of the measured partial pressure of oxygen in the blood falling below a predetermined minimum value as a part of the criterion for the detection of a tachyarrhythmia.

7. A method as claimed in claim 1 comprising the additional steps of:
   measuring a heartbeat rate of said heart; and
   utilizing said heartbeat rate as a further criterion for the detection of a tachyarrhythmia with a simultaneous presence of both criteria indicating the presence of a tachyarrhythmia.

8. A method for detecting tachyarrhythmia of the heart comprising the steps of:
   measuring a partial pressure of gases dissolved in blood in a patient and monitoring any changes of said partial pressure;
   measuring physical activity of said patient, in whom tachyarrhythmia is to be detected, utilizing an activity sensor; and
   utilizing a simultaneous occurrence of an unmodified activity level and presence of a selected change in the measured partial pressure as a criterion for the detection of a tachyarrhythmia.

9. An apparatus for detecting tachyarrhythmia of a heart comprising:
   means for measuring a partial pressure of gases dissolved in blood of a patient and monitoring any changes of said partial pressure;
   means for measuring a physical activity of said patient, in whom tachyarrhythmia is to be detected, including an activity sensor; and
   means for detecting a tachyarrhythmia comprising means for utilizing a simultaneous occurrence of a low activity level and presence of a selected change in the measured partial pressure as a criterion for the detection of a tachyarrhythmia.

10. An apparatus as claimed in claim 9 wherein said means for detecting a tachyarrhythmia comprises means for detecting a tachyarrhythmia utilizing an occurrence of a selected change in magnitude of said measured partial pressure over a selected period of time as a part of the criterion for the detection of a tachyarrhythmia.

11. An apparatus as claimed in claim 9 wherein said means for detecting a tachyarrhythmia comprises means for detecting a tachyarrhythmia utilizing an occurrence of the magnitude of said measured partial pressure falling below a predetermined minimum value as a part of the criterion for the detection of a tachyarrhythmia.

12. An apparatus as claimed in claim 9 wherein the said means for measuring a partial pressure of gases dissolved in the blood comprises means for measuring a partial pressure of oxygen in the blood.

13. An apparatus as claimed in claim 12 wherein said means for detecting a tachyarrhythmia comprises means for detecting a tachyarrhythmia by utilizing an occurrence of a decrease in magnitude of the measured partial pressure of oxygen in the blood over a selected period of time as a part of the criterion for the detection of a tachyarrhythmia.

14. An apparatus as claimed in claim 12 wherein said means for detecting a tachyarrhythmia comprises means for detecting a tachyarrhythmia by utilizing an occurrence of the magnitude of the measured partial pressure of oxygen in the blood falling below a predetermined minimum value as a part of the criterion for the detection of a tachyarrhythmia.

15. An apparatus as claimed in claim 9 further comprising:
   means for measuring heartbeat rate of said heart; and
   wherein said means for detecting a tachyarrhythmia comprises means for utilizing said heartbeat rate as a further criterion for the detection of a tachyarrhythmia with a simultaneous presence of both criteria indicating the presence of a tachyarrhythmia.

16. An apparatus for detecting tachyarrhythmia of the heart comprising:
   means for measuring a partial pressure of gases dissolved in the blood in a patient and for monitoring any changes of said partial pressure;
   means for measuring the physical activity of said patient, in whom tachyarrhythmia is to be detected, including an activity sensor; and
   means for detecting a tachyarrhythmia comprising means for utilizing the simultaneous occurrence of an unmodified activity level and a selected change in the measured partial pressure as a criterion for the detection of a tachyarrhythmia.

* * * * *